(12) United States Patent
Nakamura et al.

(10) Patent No.: US 6,780,298 B2
(45) Date of Patent: Aug. 24, 2004

(54) GAS SENSOR

(75) Inventors: Satoshi Nakamura, Okazaki (JP); Takashi Kojima, Kasugai (JP); Daisuke Makino, Ichinomiya (JP)

(73) Assignees: Denso Corporation (JP); Nippon Soken Inc. (JP)

( * ) Notice: Subject to any disclaimer, the term of this patent is extended or adjusted under 35 U.S.C. 154(b) by 0 days.

(21) Appl. No.: 10/175,090

(22) Filed: Jun. 20, 2002

(65) Prior Publication Data

US 2002/0195339 A1 Dec. 26, 2002

(30) Foreign Application Priority Data

Jun. 20, 2001 (JP) .......................... 2001-187052
May 28, 2002 (JP) .......................... 2002-154193

(51) Int. Cl.[7] .......................... G01N 27/407
(52) U.S. Cl. .......................... 204/428
(58) Field of Search .................. 204/421–429

(56) References Cited

U.S. PATENT DOCUMENTS

| 4,916,934 | A | * | 4/1990 | Nagata et al. |
| 4,929,331 | A | * | 5/1990 | Kato et al. |
| 5,073,247 | A | * | 12/1991 | Weyl |
| 5,238,552 | A | | 8/1993 | Kato et al. |
| 5,707,504 | A | * | 1/1998 | Jyouno et al. |
| 5,830,339 | A | | 11/1998 | Watanabe et al. |
| 5,880,353 | A | | 3/1999 | Graser et al. |
| 6,015,533 | A | * | 1/2000 | Young et al. |
| 6,036,829 | A | * | 3/2000 | Yamada et al. |
| 6,279,376 | B1 | | 8/2001 | Yamada et al. |
| 6,346,179 | B1 | * | 2/2002 | Makino et al. |
| 6,348,141 | B1 | * | 2/2002 | Kato et al. |

FOREIGN PATENT DOCUMENTS

| DE | 19628423 A1 | 9/1997 |
| DE | 4436580 A1 | 4/1998 |
| JP | 3-4930 | 2/1991 |
| JP | 2641346 | 5/1997 |
| JP | 2653831 | 5/1997 |
| JP | 9-127050 | 5/1997 |
| JP | 9-222416 | 8/1997 |
| JP | 11-505029 | 5/1999 |
| JP | 2000-171429 | 6/2000 |

* cited by examiner

*Primary Examiner*—Kaj K. Olsen
(74) *Attorney, Agent, or Firm*—Nixon & Vanderhye PC (57) ABSTRACT

A gas sensor is disclosed which attains high response speed, low power consumption, superior water splash resistance and a little setting direction dependency and setting angle dependency. In this gas sensor, a measured gas room is provided inside an inner cover, and gas passage holes for leading a measured gas in are provided on side surfaces of the inner cover and an outer cover. The gas passage holes provided on the outer cover are positioned much closer to a top end side than the gas passage hole provided closest to the top end side in the inner cover. Partitions disposed extendedly in an axial direction of the gas sensor are provided between the outer cover and the inner cover.

6 Claims, 10 Drawing Sheets

FIG. 1

(SECTIONAL VIEW CUT ALONG THE LINE B-B)

FIG. 2

(BOTTOM SURFACE)

FIG. 3

(SECTIONAL VIEW CUT ALONG THE LINE A-A)

(SECTIONAL VIEW CUT ALONG THE LINE C-C)

(SECTIONAL VIEW CUT ALONG THE LINE D-D)

FIG. 11

(SECTIONAL VIEW CUT ALONG THE LINE F-F)

FIG. 12

(BOTTOM SURFACE)

FIG. 13

(SECTIONAL VIEW CUT ALONG THE LINE E-E)

FIG. 14

(SECTIONAL VIEW CUT ALONG THE LINE G-G)

FIG. 15

(BOTTOM SURFACE)

FIG. 16

(SECTIONAL VIEW CUT ALONG THE LINE I-I)

FIG. 17

(BOTTOM SURFACE)

FIG. 18

(SECTIONAL VIEW CUT ALONG THE LINE H-H)

GAS SENSOR

BACKGROUND OF THE INVENTION

1. Field of the Invention

The present invention relates to a gas sensor placed in an exhaust system of an internal combustion engine and used for combustion control.

2. Description of the Prior Art

Gas sensors installed in an exhaust system of an internal combustion engine such as an automobile engine and used for combustion control include an $O_2$ sensor, an air fuel ratio sensor, an NOx sensor, an HC sensor and the like. Elements built in these gas sensors include a cup-shaped gas sensor element comprising a cup-shaped solid electrolyte, and a laminated gas sensor element constituted by laminating ceramic sheets, electrodes and the like owing to limitations such as early activation or detection principles (e.g., Japanese Patent Application Publication No. H9-127050).

The gas sensor element provided in the gas sensor must be exposed to an exhaust gas for gas density measurement, while the gas sensor element must be protected against characteristic deterioration caused by poison of the exhaust gas or against an element crack caused by water splash. For such reasons, a cover is provided for covering the gas sensor element. The cover has gas passage holes on its side surface or the like to lead the exhaust gas into a measured gas room formed inside the cover.

Incidentally, it has conventionally been known that the constitution of the cover is contrived so that the flow velocity of the exhaust gas may not have an influence on an output of the gas sensor when the exhaust gas is led into the cover from the gas passage hole (Japanese Utility Model Publication (after examination) No. H3-4930).

Furthermore, it has been known that the constitution is contrived so that it may be difficult for water spattering through an exhaust pipe in which the gas sensor is provided to get inside the cover from the gas passage hole (Japanese Patent No. 2641346, Japanese Patent Application Publication No. H9-222416).

Still further, when the element is the laminated one, in some cases, a difference arises in a positional relation between a gas flow direction and a normal direction of the gas sensor element at the time of setting the gas sensor. In this case, the cover contrived to reduce the difference of response speeds (directionality) caused by setting state is also known (Japanese Patent No. 2653831). However, the covers of conventional constitutions present a problem of slowed response speed if the directionality or water coming in is reduced.

Further yet, another problem is that the difference of the response speeds (setting angle dependency) is large when the positional relation between an axial direction of the gas sensor element and the gas flow direction is different. For example, in Japanese Patent No. 2653831 mentioned above, the gas passage holes are disposed closer to a tip end side than a gas leading part of the gas sensor, so that a gas component desired to be detected needs to reach the measured gas room by using only turbulence diffusion. Therefore, the response speed is slowed down compared to the case of the cover having the constitution that leads the gas in by using a steady flow.

Further yet, in Japanese Utility Model Publication (after examination) No. H3-4930 mentioned above, because the flow of the measured gas inside an inner cover is not uniform, the directionality occurs in the response speed, causing the difference of the response speeds to be 10 ms or more. This makes a large difference of the characteristics depending upon the setting directions of the gas sensor, which might make it impossible to expect accurate gas density measurements. In Japanese Patent No. 2641346 mentioned above, because the gas passage hole is not provided in a bottom surface part of the inner cover, the amount of gas flowing into the inner cover is small, and the response speed is therefore slowed down. Further, as the flow in the inner cover is not uniform, the directionality emerges. Further, if the area of the gas passage hole is enlarged to increase the response speed, the element crack due to the water splash is more likely to occur, and moreover, when the element is heated by a heater to keep a constant temperature, there is a problem of increased power consumption.

Incidentally, in German Patent No. 19628423A1, the side surface of an outer cover does not have the gas passage holes, and it is designed to lead the gas that will flow into the inner cover from the gas passage hole provided on the bottom surface of the outer cover. However, because this gas passage hole is vertical to the gas flow, it has resistance to the gas inflow and poses a problem of the slowed response speed. Further, if a tip end portion of the element is set inclining to a downstream side of the exhaust gas flow, it raises a problem of the slowed response speed, and if it is set inclining to an upstream side, it raises a problem of deteriorated water splash resistance.

In both of German Patent No. 19628423A1 and German Patent No. 4436580A1, because the inner cover projects from the outer cover, the inner cover is exposed directly to the gas flow, and therefore the inner cover is cooled down. Since a radiant heat quantity from the gas sensor element is proportionate to the fourth power of the temperature of the inner cover, the power consumption increases when the inner cover is cooled down.

In Japanese Patent Application Publication No. H9-222416, since the bottom surface of the inner cover and the bottom surface of the outer cover are kept away, the exhaust gas that has got in from the gas passage hole on the side surface of the outer cover flows out from the gas passage hole on the bottom surface of the outer cover. This reduces the amount of gas flowing into the inner cover, and the response speed is thus slowed down.

In Japanese Patent Application Publication No. 2000-171429, if the tip end portion of the element is set inclining to the downstream side or the upstream side toward the flow of the exhaust gas, it raises a problem that responsiveness is slowed down. In other words, the setting angle dependency is increased, giving trouble in setting operation of the gas sensor.

SUMMARY OF THE INVENTION

The present invention has been made in view of such conventional problems, and is intended to provide a gas sensor with a high response speed, low power consumption, superior water splash resistance and a little setting direction dependency and setting angle dependency.

One aspect of the present invention is in a gas sensor comprising a gas sensor element and a cylindrical housing for inserting and fixing said gas sensor element, measured gas side covers having a bottom and provided on a tip end side of said housing and an atmosphere side cover provided on a base end side, wherein said measured gas side covers comprises an inner cover for directly covering the gas sensor element and an outer cover directly exposed to measured gas ambience, and are provided with a measured gas room inside said inner cover;

gas passage holes for leading a measured gas into said measured gas room are provided on side surfaces of said inner cover and said outer cover respectively, and the gas passage hole provided on said outer cover is disposed in a position much closer to the tip end side than the gas passage hole provided closest to the tip end side in said inner cover; and partitions disposed extendedly in an axial direction of the gas sensor are provided between said outer cover and said inner cover.

Next, functional effects of the present invention will be described. In the gas sensor in accordance with the present invention, the partitions disposed extendedly in an axial direction are provided between the outer cover and the inner cover, and consequently, it is possible to prevent the measured gas that has got in from the gas passage hole on the outer cover from passing other gas passage holes to flow out of the outer cover again, and further possible to rectify a gas flow between the outer cover and the inner cover so that the measured gas can quickly reach the gas passage hole on the inner cover along the partitions. In this way, since the measured gas can quickly reach the measured gas room inside the inner cover, it is possible to make the response speed of the gas sensor faster.

Furthermore, since the partitions function as guide plates of the measured gas, the measured gas can be led from the gas passage holes to the measured gas room always in the same state, without depending upon the setting direction and setting angle of the gas sensor.

Still further, the gas passage hole provided on the outer cover is disposed in a position much closer to the tip end side than the gas passage hole provided closest to the tip end side in the inner cover. This makes it possible to prevent the gas passage holes on the outer cover and those on the inner cover from being in a confronting state, and thus both the flow holes will be in a communicating state, thereby preventing water drops from getting in from the outside. This means that when the water drops get in from the gas passage hole of the outer cover, it is difficult for the water drops to reach the gas sensor element in the measured gas room by the blocking of the inner cover. In this way, the gas sensor in accordance with the present invention has high water splash resistance.

Further yet, as it is not necessary to enlarge the diameter of the gas passage holes to enhance responsiveness, the inflow amount of the gas can be controlled, and as heat taken away from the gas sensor element is reduced, it is possible to reduce the power consumption of the heater for heating the gas sensor element.

As described above, according to the present invention, it is possible to provide the gas sensor with the high response speed, low power consumption, superior water splash resistance and a little setting direction dependency and setting angle dependency.

Furthermore, in the gas sensor of the present invention, it is preferable that the gas passage holes to be provided in the outer cover and the inner cover satisfy the following requirements:

First, it is preferable that the gas passage holes to be provided on the side surfaces of the outer cover and the inner cover are each of the same shape. It is possible to equalize the inflow amount of the measured gas in each gas passage hole by making gas passage holes uniform, so that the dependency on the setting angle can be reduced.

Furthermore, it is preferable that two or more and eight or less gas passage holes are provided. In this way, the gas flows in equally from each hole, and the setting directionality can be reduced. Only one gas passage hole might cause the direction dependency, and if nine or more gas passage holes are provided, manufacturing costs of the covers might be increased.

Still further, it is preferable that the gas passage holes are provided at equal intervals in a circumferential direction of the cover. This can reduce the setting direction dependency.

Further, it is preferable that the above gas passage holes are arranged evenly at the same height in the axial direction. By arranging the gas passage holes evenly at the same height in the axial direction, it is possible to reduce the setting angle dependency and the setting direction dependency.

Figure 1:
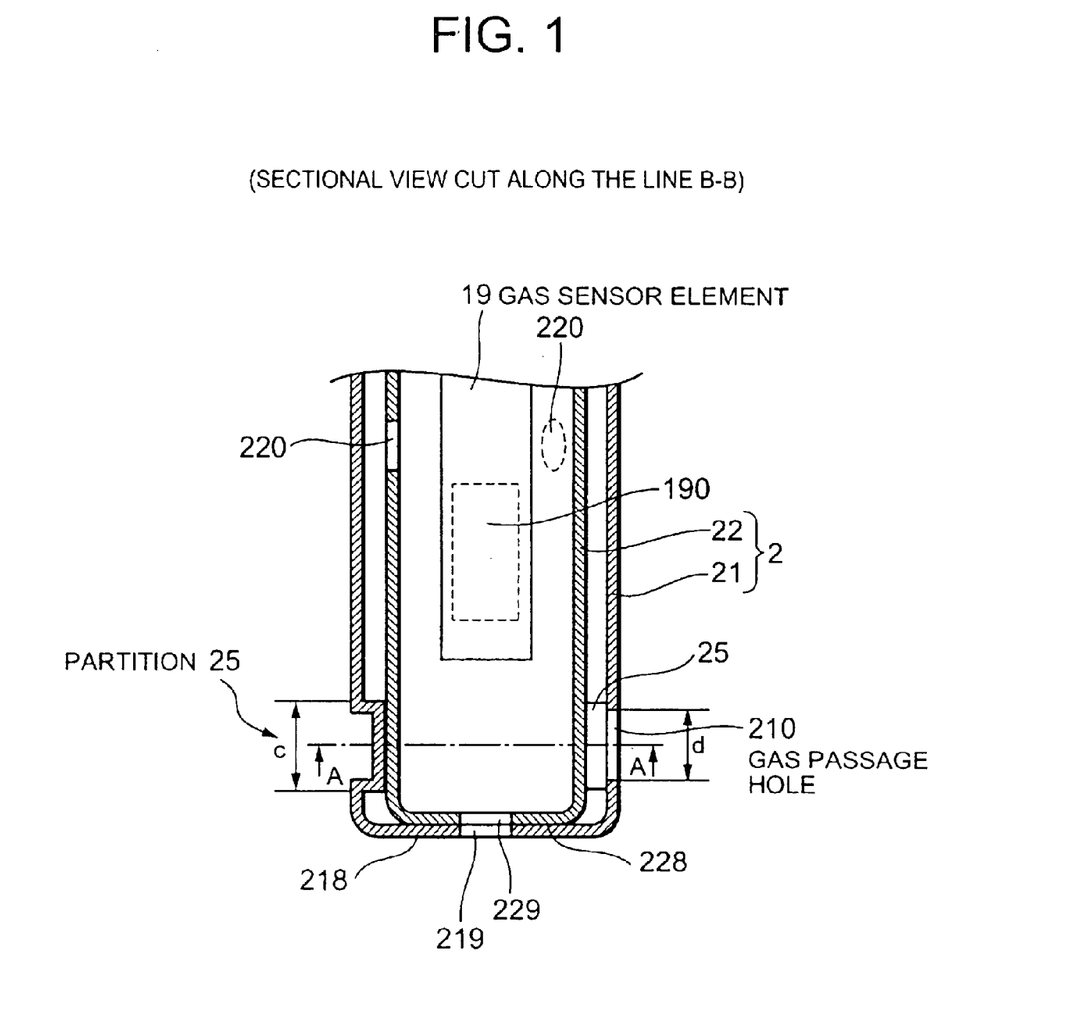
FIG. 1 is an explanatory view in section of essential parts in an axial direction in the vicinity of measured gas side covers of a gas sensor, in an embodiment 1 (sectional view cut along the line B—B of FIG. 2).

Further yet, in the gas sensor of the present invention, the gas sensor element can be applied to one that use a cup-shaped element (see FIG. 14) besides a laminated element, as shown in FIG. 1. However, by applying the present invention to the laminated element that is more fragile, the present invention functions more effectively.

Next, as one aspect of the present invention, it is preferable that the partitions are constituted in a way to project from the inner surface of the outer cover to the inner cover in the sectional diameter direction of the gas sensor. This makes it possible to prevent the measured gas that has got in from the gas passage hole on the outer cover from passing other gas passage holes to flow out of the outer cover again, and further possible to rectify the gas flow between the outer cover and the inner cover so that the measured gas can quickly reach the gas passage hole of the inner cover along the partitions. In this way, since the measured gas can quickly reach the measured gas room inside the inner cover, it is possible to make the response speed of the gas sensor faster.

Next, as one aspect of the present invention, it is preferable that the partitions are constituted in a way to project from the outer surface of the inner cover to the outer cover in the sectional diameter direction of the gas sensor. This integrates the partitions with the inner cover, thereby lowering the setting cost of the partitions.

Furthermore, the gas flow can be rectified between the outer cover and the inner cover so that the measured gas that has got in from the gas passage hole on the outer cover may be prevented from passing other gas passage holes to flow out of the outer cover again, and that the measured gas can quickly reach the gas passage hole of the inner cover along the partitions. In this case, since the measured gas can quickly reach the measured gas room inside the inner cover, it is possible to make the response speed of the gas sensor faster.

Next, as one aspect of the present invention, it is preferable that the projection height of the partitions is $1/3$ or more of a clearance between the inner surface of the outer cover and the outer surface of the inner cover. This makes it possible to enlarge a component in an axial direction of the gas flow between the inner cover and the outer cover.

Furthermore, when the projection height is below $1/3$ of the clearance, the component in the axial direction of the gas flow is not very large, which might result in insufficient rectification effects to retain the setting direction dependency and setting angle dependency.

The projection height is the distance between the inner surface of the outer cover and the inner surface of the partition. The clearance is the distance between the outer surface of the inner cover and the inner surface of the outer cover. Examples of these are indicated as a, b in the drawings of each Embodiment.

Next, as one aspect of the present invention, it is preferable that the axial length of the partitions is ½ or more of the axial length of the gas passage hole. This makes it possible to enlarge the component in the axial direction of the gas flow between the inner cover and the outer cover.

If the axial length is shorter than ½, the measured gas might pass other gas passage holes to flow out of the outer cover again.

An upper limit of the axial length will be described later.

Next, as one aspect of the present invention, it is preferable that each of the partitions is provided between two adjacent gas passage holes made on the outer cover such that the partitions are circumferentially arranged. In this way, the gas flow can further be rectified between the outer cover and the inner cover, thereby making it possible to obtain more of the effects in accordance with the present invention.

Next, as one aspect of the present invention, it is preferable that the partitions are provided in the circumferential gaps communicating with the plurality of gas passage holes made on the outer cover, and that the axial length of the partitions is ½ or more of the axial length of the gas passage hole. This makes it possible to further rectify the gas flow between the outer cover and the inner cover, thereby allowing not only to obtain more of the effects in accordance with the present invention but also to enlarge the component in the axial direction of the gas flow between the inner cover and the outer cover. If the axial length is shorter than ½, the measured gas might pass other gas passage holes to flow out of the outer cover again.

Next, as one aspect of the present invention, it is preferable that the partitions are constituted of concave parts made toward the inside in a sectional diameter direction on the side surface of the outer cover.

Furthermore, as one aspect of the present invention, it is preferable that the partitions are projections provided in the circumferential gaps communicating with the plurality of gas passage holes made on the side surface of the outer cover, and that these projections provide cuts on part of the side surface of the outer cover, and the partitions are constituted by bending the cut part. In this case, the partitions can be made integrally with the outer cover by applying punching-bending forming to the outer cover, thereby making it possible to reduce processing work and material costs.

Next, as one aspect of the present invention, it is preferable that an end portion of the partitions on the base end side in an axial direction of the gas sensor does not reach the gas passage hole provided on the inner cover. In this case, however relative positions of the inner cover and the outer cover in a diametric direction, which are rectangular to the axial direction of the gas sensor, may be determined, the flow of the measured gas is not obstructed and the responsiveness is difficult to get worse.

That is, the responsiveness hardly changes between the case where the outer cover is set to the inner cover at a predetermined angle and the case where the outer cover is set as a position at which the outer cover is rotated at an arbitrary angle from the predetermined angle above. Therefore, it is not necessary to determine the positional relations of the inner cover and the outer cover when both the covers are set, thereby making possible to lower setting cost.

If the end portion of the partitions on the base end side reaches the gas passage hole on the inner cover, in other words, since the end portion of the partitions on the base end side overlaps the gas passage hole on the inner cover, the responsiveness might get worse. In order to prevent this, it is necessary to contrive in such a way as to set the outer cover in a position not to obstruct the gas flow to the gas passage hole of the inner cover, which might increase the setting cost.

Next, as one aspect of the present invention, it is preferable that the gas sensor element is board-shaped, and that its sectional shape in a diametric direction of the inner cover is elliptic or square. This makes it possible to reduce not only the capacity in the inner cover but also the capacity of the measured gas room formed inside the cover. Thus, the responsiveness of the gas sensor can be enhanced.

Next, as one aspect of the present invention, it is preferable that the axial distance along the axial direction of the gas sensor between the gas passage hole provided closest to the tip end side on the inner cover and the gas passage hole provided closest to the base end side on the outer cover is 5 mm or more. This can prevent the water drops that have got in from the gas passage hole on the side surface of the outer cover from getting inside the cover from the gas passage hole of the inner cover. At this time, the water drops are discharged from the gas passage hole on the outer cover different from the gas passage hole through which the water drops has got into, or the water drops evaporate in the gap between the outer cover and the inner cover. If the axial distance is below 5 mm, the water drops that have got in from the gas passage hole of the outer cover get inside the inner cover, which might lead to the element crack caused by the water splash or the like.

Next, as one aspect of the present invention, it is preferable that the outer cover and the inner cover are in a shape having a bottom, and the distance between bottom surfaces of both covers are in a range of 0 to 5 mm. This can prevent the measured gas that has got in from the gas passage hole on the outer cover from directly getting out from an opening of the bottom surface, thereby allowing the response speed to be faster.

If the distance between the bottom surfaces exceeds 5 mm, the gas that has got in from the gas passage hole on the outer cover might directly get out from the opening of the bottom surface. The distance between the bottom surfaces is the distance between the inner surface of the outer cover and the outer surface of the inner cover.

DETAILED DESCRIPTION OF THE PREFERRED EMBODIMENTS

Embodiment 1

An embodiment of a gas sensor in accordance with the present invention will be described with FIG. 1 to FIG. 8. As shown in FIG. 1 to FIG. 4, the gas sensor comprises a gas sensor element 19 and a cylindrical housing 10 for inserting and fixing the gas sensor element 19, measured gas side covers 2 having a bottom and provided on a tip end side of the housing 10 and an atmosphere side cover 31 provided on a base end side, and an upper cover 32. The measured gas side covers 2 comprise an inner cover 22 for directly covering the gas sensor 19 and an outer cover 21 directly exposed to measured gas ambience.

A measured gas room 20 is provided inside the inner cover 22, and on side surfaces of the inner cover 22 and the outer cover 21, gas passage holes 210 and 220 are each provided which are for leading a measured gas into the measured gas room 20.

Figure 4:
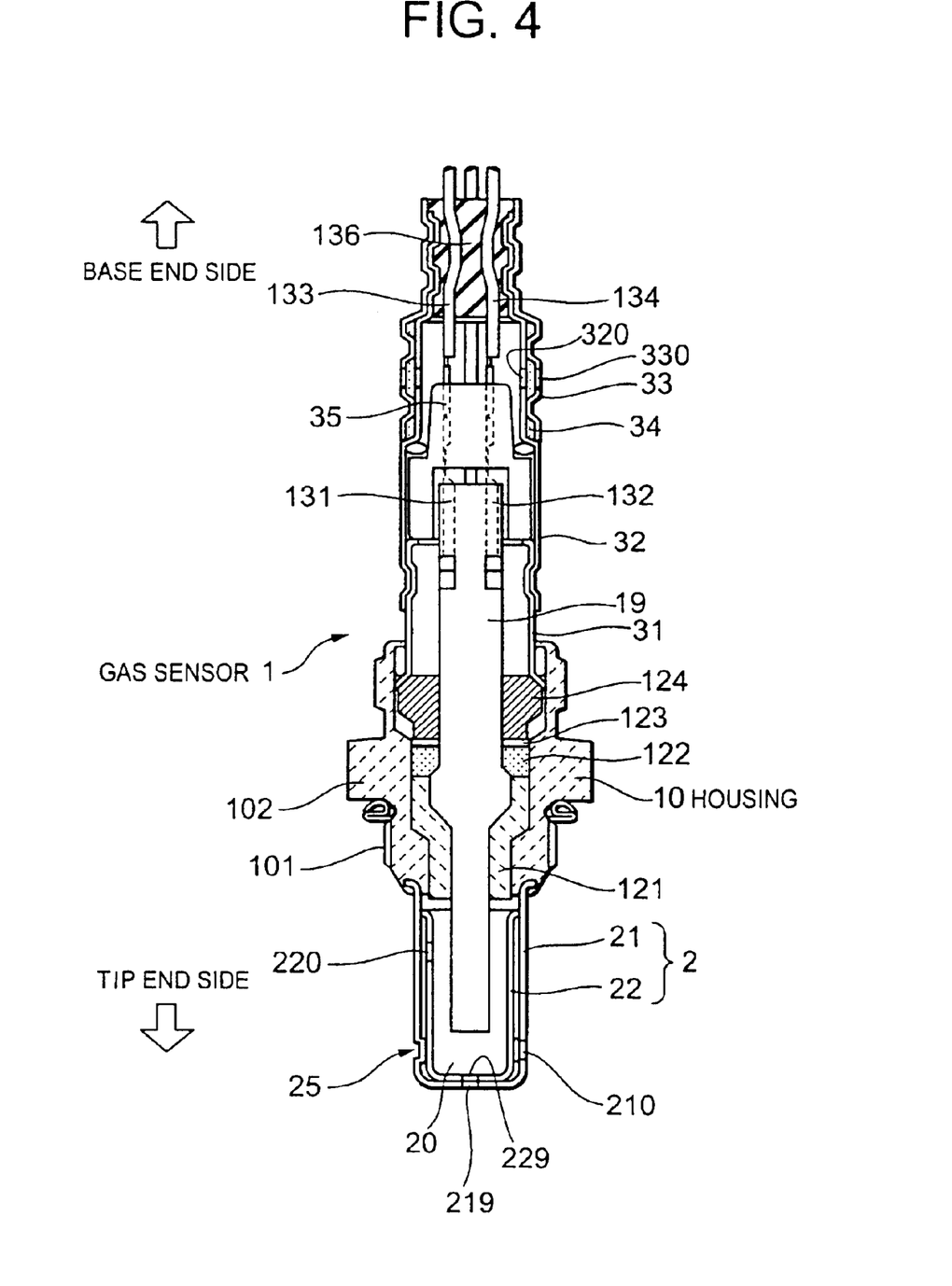
FIG. 4 is an explanatory view in section of the gas sensor in the embodiment 1.

The gas passage hole 210 provided on the outer cover 21 is disposed in a position much closer to the tip end side (lower part of the drawings in FIG. 1 and FIG. 4 is the tip end side) than the gas passage hole 220 provided closest to the tip end side in the inner cover 22. Between the outer cover 21 and the inner cover 22, partitions 25 disposed extendedly in an axial direction of the gas sensor are provided.

Hereafter, it will be described in detail. A gas sensor 1 in accordance with present embodiment is set in an exhaust system of an automobile engine, and used for combustion control of the engine. An exhaust gas is led in as the measured gas, and as shown in FIG. 1, the gas sensor element 19 constituted to detect oxygen density in the exhaust gas is built in. A reference numeral 190 in accordance with FIG. 1 indicates a gas detector unit.

As shown in FIG. 4, the measured gas side covers 2 constituted doubly of the outer cover 21 and the inner cover 22 are connected to the tip end side of the cylindrical housing 10, and the atmosphere side cover 31 is connected to the base end 20 side of the housing 10. On a body of the housing 10, a screw part 101 is provided which is screwed into a screw hole disposed in the exhaust system in which the gas sensor 1 is placed. Further, a flange part 102 that contacts the exhaust system is provided.

The gas sensor element 19 is inserted and disposed in the housing 10. Between the gas sensor element 19 and an inner surface of the housing 10, an electrical porcelain 121, a powder 122, a packing 123 and an insulator 124 are filled. In addition, the measured gas room 20, which will be indicated below, and the atmosphere side ambience in the atmosphere side cover 31 and the upper cover 32 that are on the base end side of the gas sensor 1, are airtightly separated by the powder 122 or the like. The atmosphere side cover 31 is directly connected to the housing 10. The upper cover 32 is connected to the base end side of the atmosphere side cover 31. An electrical porcelain 35 is provided inside the upper cover 32.

Furthermore, an outer cover 33 is provided on the base end side of the upper cover 32 via a water-repellent filter 34. Atmosphere leading holes 330 and 320 are disposed in a position where the upper cover 32 and the outer cover 33 confront the water-repellent filter 34, through which the atmosphere is led into the atmosphere side ambience formed inside the upper cover 32 and the atmosphere side cover 31. Further, a rubber bush 136 is provided inside the base end side of the upper cover 32.

Furthermore, in order to take out outputs from the gas sensor element 19, or to electrify a heater (not shown) built in the gas sensor element 19, lead wires 133 and 134 are extendedly provided on the outside of the gas sensor 1 via connectors 131 and 132. Four connectors and four lead wires are given to the gas sensor 1 in the present embodiment. However, because parts of them are in positions where they can not be seen in the drawing, they are omitted from the description.

Next, the measured gas side covers 2 will be described as shown in FIG. 1 to FIG. 4.

The measured gas side covers 2 in the present embodiment have a double constitution comprising the outer cover 21 and the inner cover 22. Both of the covers 21 and 22 are cylindrical and have bottoms, and their sectional shape is circular. Both of them are provided with the gas passage holes 210 and 220 on the side surfaces, and gas passage holes 219 and 229 are provided also in the centers of bottom surfaces 218 and 228. The bottom surface 228 of the inner cover 22 and the bottom surface 218 of the outer cover 21 are joined by spot welding. The gas passage holes 219 and 229 on the bottom surfaces 218 and 228 of each cover 21 and 22 are overlapped. Further, the section of the gas sensor element 19 is rectangular, and an axial center of the gas sensor element 19 and the axial center of measured gas side covers 2 are disposed in a way to correspond to each other, and the corresponded axial center is G (see FIG. 3).

Figure 3:
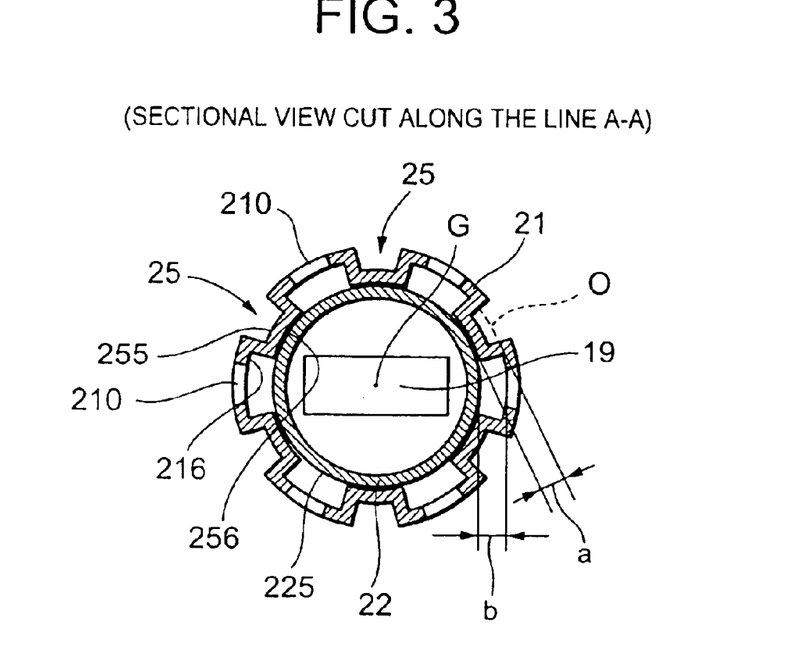
FIG. 3 is an explanatory view in section of the gas sensor in a diametric direction in the embodiment 1 (sectional view cut along the line A—A of FIG. 1).

As shown in FIG. 1 and FIG. 3, the gas passage hole 210 provided on the side surface is disposed in a position such that the distance between the center of the gas passage hole 210 and the bottom surface 218 along the axial center of the gas sensor element 19 is 4 mm. This distance may vary depending on the distance between the end portion position on the tip end side of the gas passage hole 210 and the bottom surface 218. Further, the gas passage hole 210 is circular and has a diameter of 2 mm, and six gas passage holes 210 are arranged in line at equal intervals in a circumferential direction.

Figure 2:
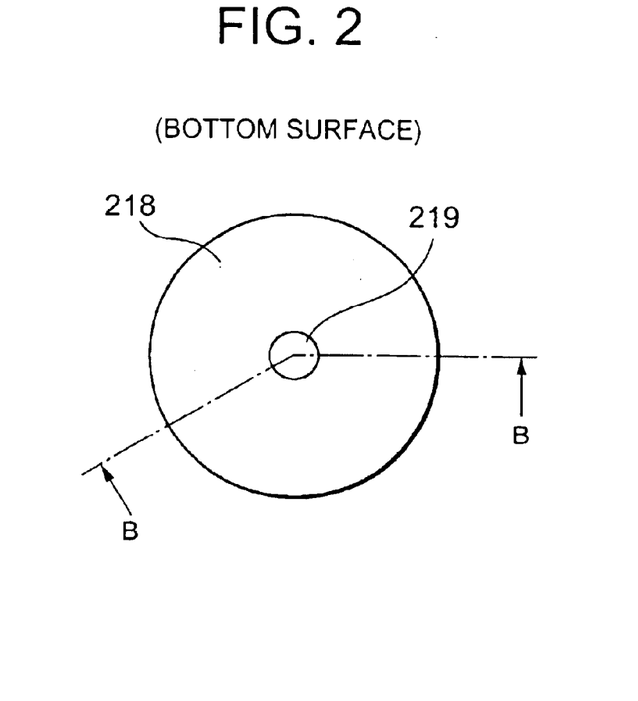
FIG. 2 is a plan view showing a bottom surface of the measured gas side covers in the embodiment 1.

As shown in FIG. 2, the gas passage hole 219 provided on the bottom surface 218 is a circular hole having a diameter of 2 mm in the center of the bottom surface 218, and one gas passage hole 219 is provided.

As shown in FIG. 3, between each of six gas passage holes 31 provided on the side surface, six partitions 25 are provided which project toward the inner cover 22.

The shape of the partitions 25 is rectangular and has a size of 2 mm in the circumferential direction and 4 mm in the axial direction, and their projection height a is 0.8 mm. A clearance b between the inner cover 22 and the outer cover 21 is 1 mm. The projection height a is the distance between an inner surface 216 of the outer cover 21 and an inner surface 256 of the partition 25 (symbol O indicates an extension line that extends the inner surface 216 up to the position of the partition 25).

The partitions 25 in the present embodiment are formed by applying press forming to corresponding parts of the outer cover 21 and producing concave parts that project to the side of the inner cover 22 in the diametric direction. In addition, the clearance b is the distance between an outer surface 225 of the inner cover 22 and the inner surface 216 of the outer cover 21. As shown in FIG. 1, an axial length c of the partitions 25 is 4 mm, and an axial length d of the gas passage hole 210 is 2 mm.

The axial length c of the partitions 25 is measured by the distance of the side facing the inner cover 22. The same applies to the axial length d of the gas passage hole 210. Further, the gas passage hole 220 provided on the side surface of the inner cover 22 is disposed in a position at a height of 15 mm from the bottom surface 228. This is based on the distance between the end portion position on the tip end side of the gas passage hole 220 and the bottom surface 228.

In the gas sensor element 19, spots that function as the gas detector unit 190 are within a range of about 6 to 10 mm from the bottom surface 228, and the gas passage hole 220 is positioned closer to the base end side than the gas detector unit 190.

The gas flow of the exhaust gas that is the measured gas in the gas sensor 1 in the present embodiment will be described. The flow of the measured gas that gets in from the gas passage hole 210 provided on the side surface of the outer cover 21 is restricted by the partitions 25, so that the exhaust gas scarcely flows out directly to the outside from the gas passage holes 210 other than the gas passage hole 210 from which the exhaust gas has flown in.

The measured gas that has flown in from one gas passage hole 210 flows to the base end side in an axial direction, and then gets into the measured gas room 20 formed inside the inner cover 22 from the gas passage hole 220 provided on the side surface of the inner cover 22. Since the bottom surfaces 218 and 228 of both the covers 21 and 22 are hermetically stuck and have no distance, the measured gas scarcely flows toward the tip end side.

Next, performance of the gas sensor 1 in the present embodiment will be described. The gas sensor having the partitions in accordance with the present embodiment and the gas sensor that is of the same type as the former one but does not have the partitions are each set in a pipe of the actual automobile engine, and the setting angle at this time is changed every 15 in a range of −30 to +30. The setting angle is the angle formed by a normal direction of the pipe that constitutes the exhaust system and the axial direction of the gas sensor.

Figure 5:
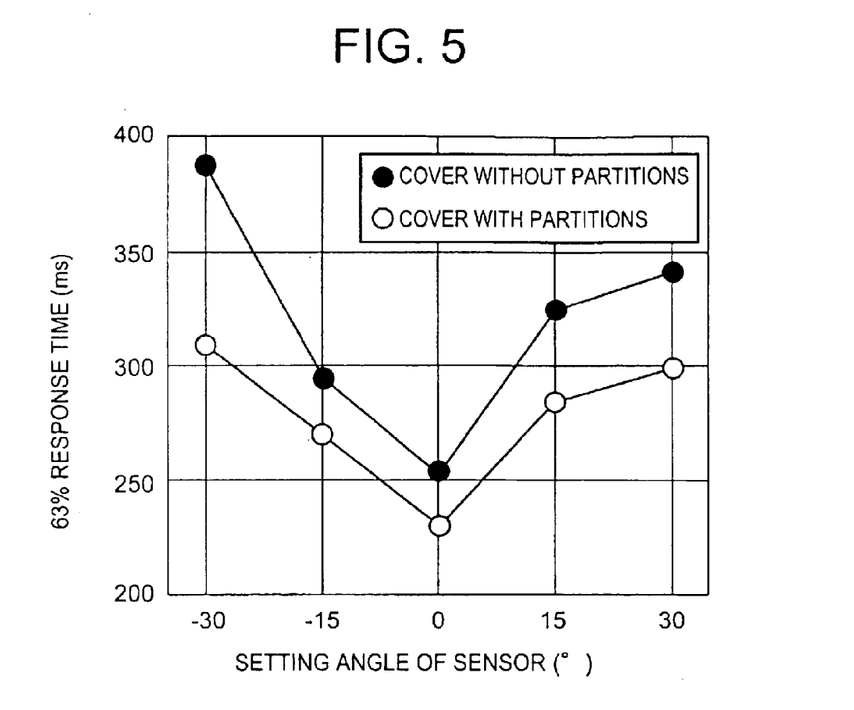
FIG. 5 is a diagram showing the relation among the presence of a partition, a setting angle and a 63% response time.

The engine is started in this state, and the 63% response time when the combustion state of the engine is switched from rich to lean is measured. The measurement results are indicated in FIG. 5. According to FIG. 5, the farther the setting angle is away from 0, the worse the responsiveness becomes. However, it is evident that in any state the gas sensor with the partitions has the shorter response time and superior response.

Figure 6:
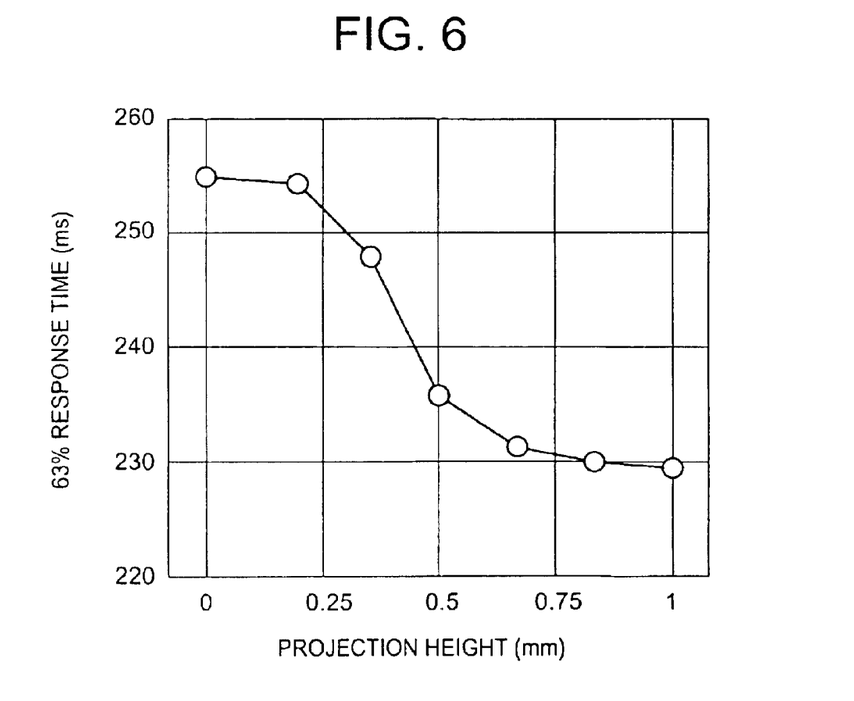
FIG. 6 is a diagram showing the relation between the projection height of the partition and the 63% response time.

Furthermore, several gas sensors different in the projection heights of the partitions are prepared, and the 63% response time is measured for each of them in the same way as above. The measurement results of these are indicated in FIG. 6. A projection height of 0 mm indicates the state of no partitions, and a projection height of 1 mm indicates the state in which the partitions 25 hermetically stick to an outer surface 226 of the inner cover 22. When the partitions 25 have a height of 1 mm, the clearance is 0 between both the covers 21 and 22 in the part where the partitions 25 are provided, so that both the covers 21 and 22 are partitioned by the partitions 25.

According to FIG. 6, it is evident that the response time is short and the responsiveness is low when the projection height of the partitions is low, and that the higher the projection height becomes, the better the responsiveness becomes. Further, it is evident that when the projection height becomes ⅓ or more of the clearance, the responsiveness is especially enhanced.

Next, the functional effects of the gas sensor in the present embodiment will be described. The gas sensor in the present embodiment is provided with the partitions 25 disposed extendedly in the axial direction between the outer cover 21 and the inner cover 22. Consequently, the measured gas that has got in from the gas passage hole 210 on the outer cover 21 can be prevented from passing other gas passage holes 210 to flow out of the outer cover 21 again, and moreover, the gas flow can be rectified between the outer cover 21 and the inner cover 22 so that the measured gas can quickly reach the gas passage hole 220 on the inner cover 22 along the partitions 25. In this way, the measured gas can reach the measured gas room 20 inside the inner cover 22, thereby enabling the response speed of the gas sensor 1 to be faster.

Furthermore, since the partitions 25 function as guide plates of the measured gas, the measured gas can be led into the measured gas room 20 from the gas passage holes 210 and 220 always in the same state, without depending upon the setting direction and the setting angle of the gas sensor 1. As a result, it is possible to obtain gas responsiveness that is not dependent upon the setting direction and the setting angle.

Still further, the gas passage hole 210 provided on the outer cover 21 is disposed in a position closer to the tip end side than the gas passage hole 220 provided closest to the tip end side in the inner cover 22. This makes it possible to prevent the gas passage holes 210 and 220 on both the covers 21 and 22 from being in a confronting state, and to prevent water drops from getting in from the outside. In this way, the gas sensor in accordance with the present embodiment has high water splash resistance.

In particular, in the case where the water drops collected in the pipe of the exhaust system right after the start of the engine splash onto the measured gas side covers 2 of the gas sensor 1, the water drops do not reach the gas detector unit 190 if the gas passage hole 210 on the outer cover 21 and the gas passage hole 220 on the inner cover 22 are kept away in the axial direction, thereby making it possible to prevent the crack of the gas sensor element 19 caused by the water splash. Further, as it is not necessary to enlarge the diameter of the gas passage hole to enhance the responsiveness, the inflow amount of the gas can be restricted, and as heat taken away from the gas sensor element is reduced, it is possible to reduce the power consumption of the heater for heating the gas sensor element.

Figure 7:
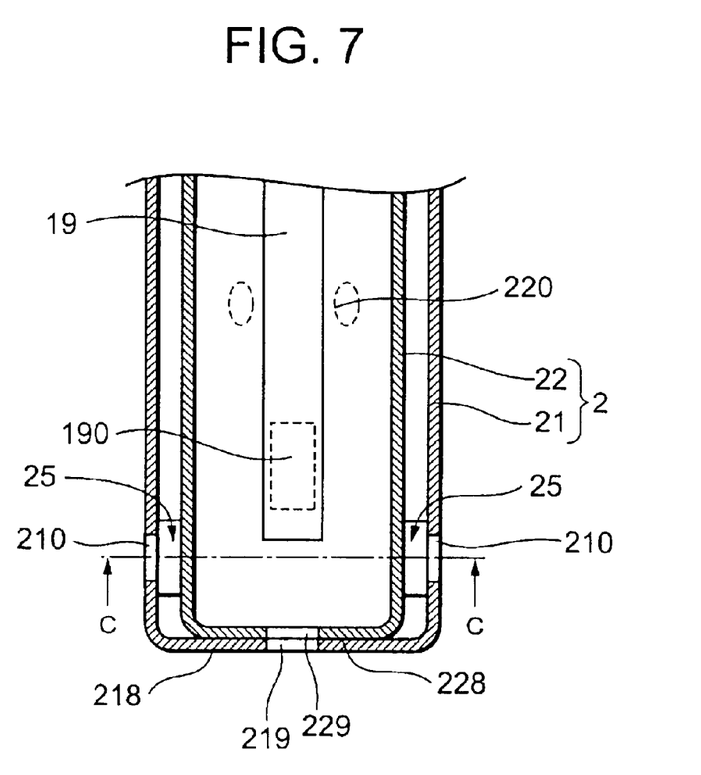
FIG. 7 is an explanatory view in section of essential parts in an axial direction in the vicinity of the measured gas side covers in which a section of the inner cover is elliptic, in the embodiment 1.
Figure 8:
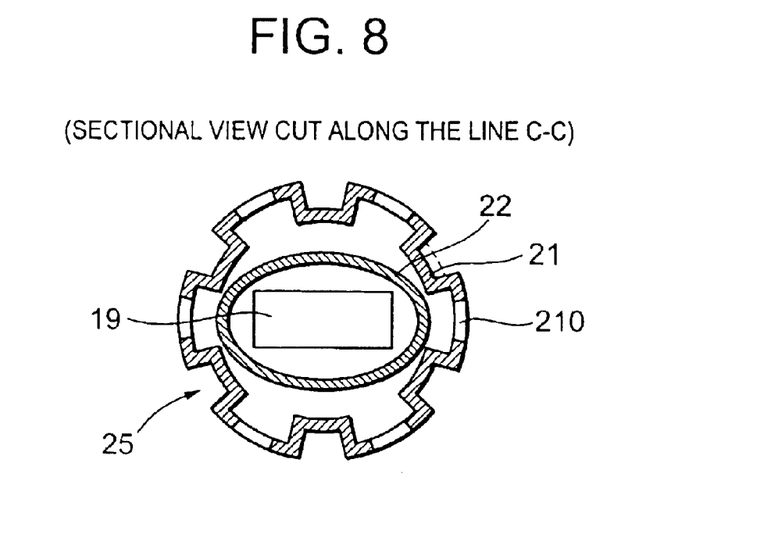
FIG. 8 is an explanatory view in section of essential parts in a diametric direction in the vicinity of the measured gas side covers in which the section of the inner cover is elliptic, in the embodiment 1 (sectional view cut along the line C—C of FIG. 7).

As described above, according to the present embodiment, it is possible to provide the gas sensor with the high response speed, low power consumption, superior water splash resistance and a little setting direction dependency and setting angle dependency. Further, as shown in FIG. 7 and FIG. 8, when the sectional shape of the inner cover 22 is elliptic, it is also possible to have the same effects as in the present embodiment. In addition, the gas sensor of this shape in particular can reduce the capacity of the measured gas room formed inside the cover since its sectional shape made elliptic, thereby making it possible to have the gas sensor with higher responsiveness.

Embodiment 2

Figure 9:
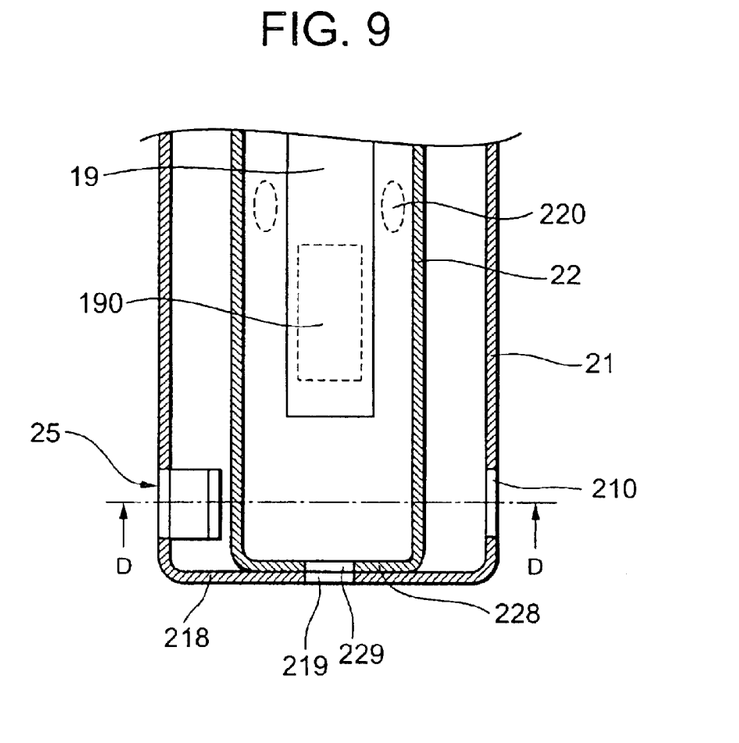
FIG. 9 is an explanatory view in section of essential parts in an axial direction in the vicinity of the measured gas side covers having the partitions constituted by bending an outer cover, in an embodiment 2.
Figure 10:
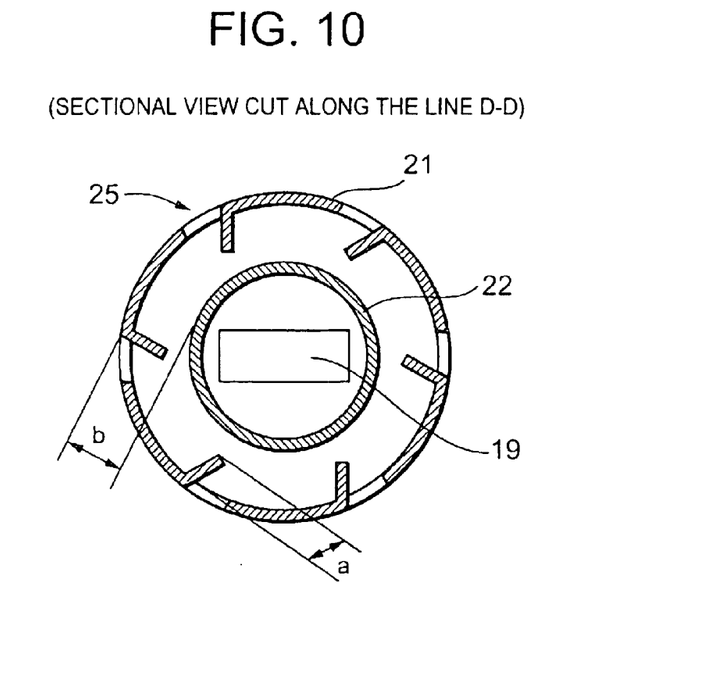
FIG. 10 is an explanatory view in section of the gas sensor in a diametric direction in the embodiment 2 (sectional view cut along the line D—D of FIG. 9).

As shown in FIG. 9 and FIG. 10, in the gas sensor in accordance with the present embodiment, the partitions 25 are constituted by making cuts on part of the side surface of the outer cover 21 and bending the cut part. Further, the partitions 25 are provided between one gas passage hole 210 and another adjacent gas passage hole. The projection height a of the partitions 25 is 0.8 mm, and the clearance b is 1 mm. The others are the same as in Embodiment 1, and the functional effects are also the same.

Embodiment 3

Figure 11:
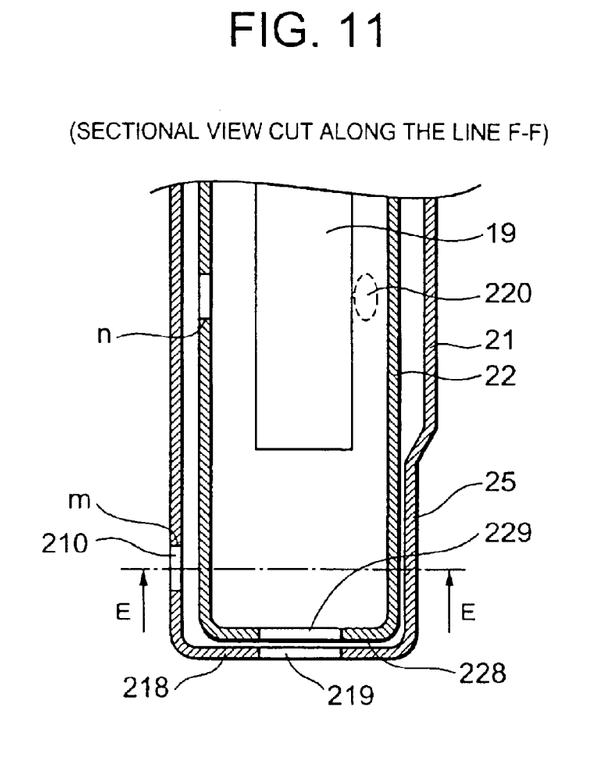
FIG. 11 is an explanatory view in section of essential parts in an axial direction in the vicinity of the measured gas side covers whose partitions are V-shaped, in an embodiment 3 (sectional view cut along the line F—F of FIG. 12).
Figure 12:
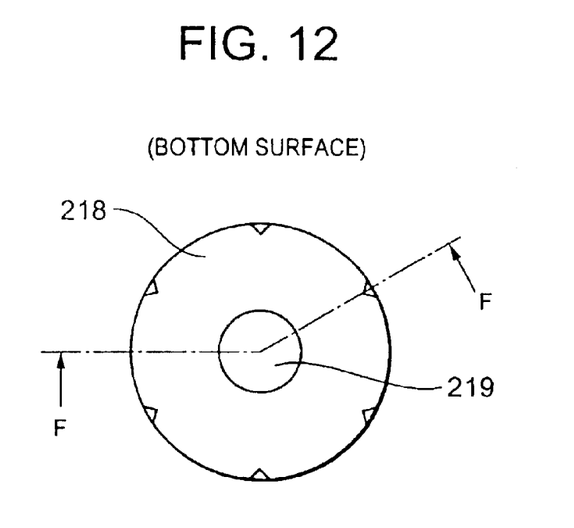
FIG. 12 is a plan view showing the bottom surface of the measured gas side covers in the embodiment 3.
Figure 13:
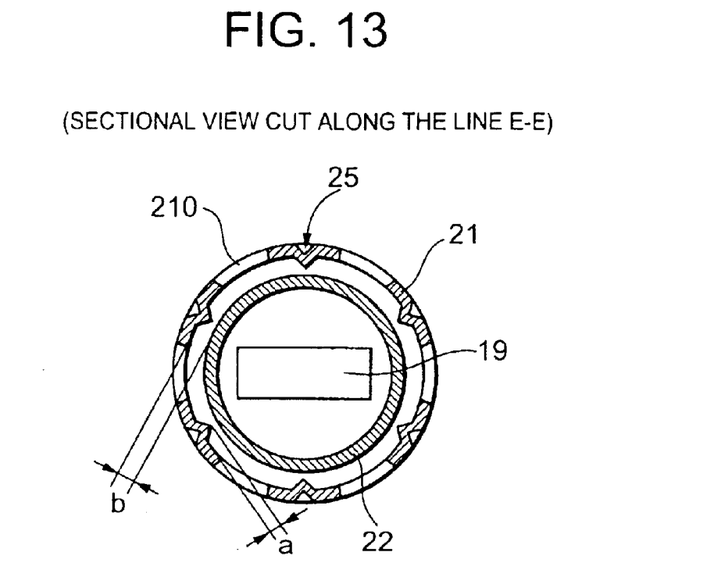
FIG. 13 is an explanatory view in section of the gas sensor in a diametric direction, in the embodiment 3 (sectional view cut along the line E—E of FIG. 11).

As shown in FIG. 11 to FIG. 13, in the gas sensor in the present embodiment, the outer cover 21 is hollowed on its side surface to be V-shaped when seen in terms of the sectional shape in the diametric direction, from the top end (vicinity of the bottom surface) of the outer cover 21 to a position to surpass a portion m of the gas passage hole 210 on the outer cover 21 and not to reach a portion n of the gas passage hole 220 on the inner cover 22, whereby the partitions 25 are formed. Further, the partitions 25 are disposed in all parts between the adjacent gas passage holes 210 on the outer cover 21. The projection height a of the partitions 25 is 0.8 mm, and the clearance b is 1 mm. The others are the same as in Embodiment 1, and the functional effects are also the same.

Embodiment 4

Figure 14:
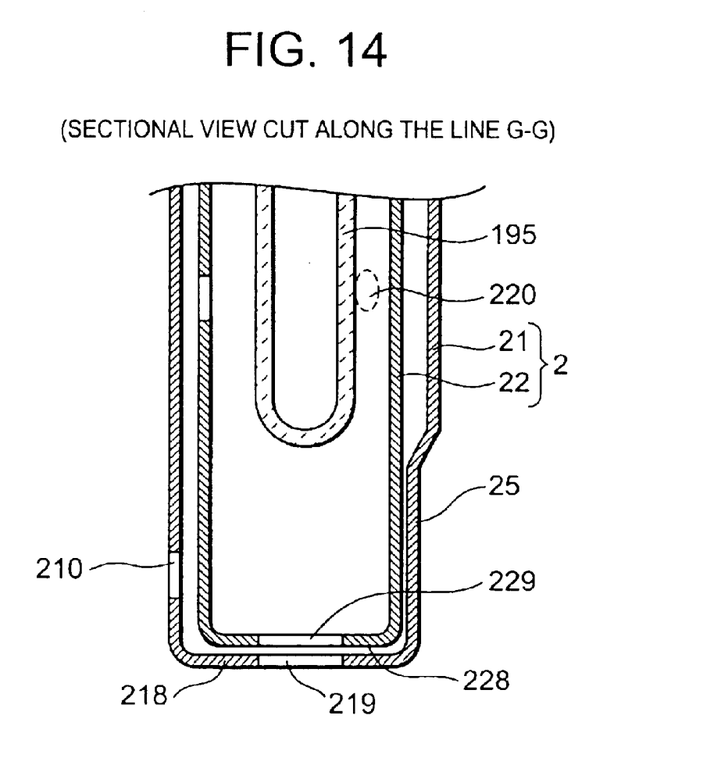
FIG. 14 is an explanatory view in section of essential parts in an axial direction in the vicinity of the measured gas side covers whose gas sensor element is cup-shaped, in an embodiment 4.
Figure 15:
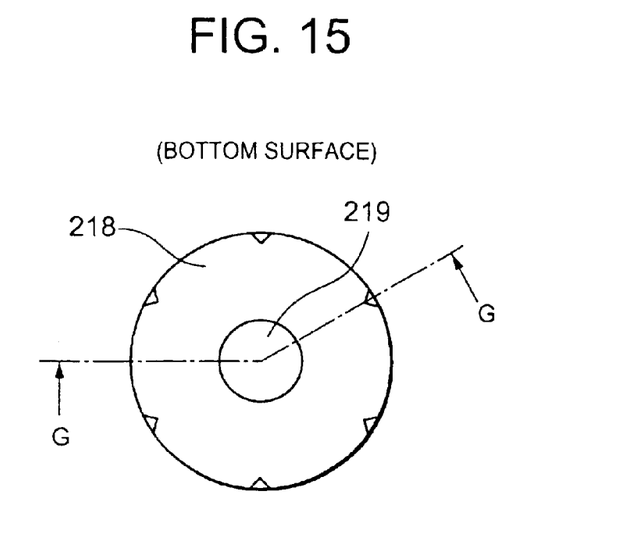
FIG. 15 is a plan view showing the bottom surface of the measured gas side covers in the embodiment 4.

As shown in FIG. 14 and FIG. 15, the gas sensor in accordance with the present embodiment comprises a cup-shaped gas sensor element 195 made from a solid electrolyte that is cylindrical and has a bottom. The measured gas side covers 2 comprising the outer cover 21 and the inner cover 22, and the partitions 25 are of the same shape as those in Embodiment 3. The axial center of the cup-shaped gas sensor element 195 and the axial center of the measured gas side covers 2 are disposed to correspond to each other. The others are the same as in Embodiment 1, and the functional effects are also the same.

Embodiment 5

Figure 16:
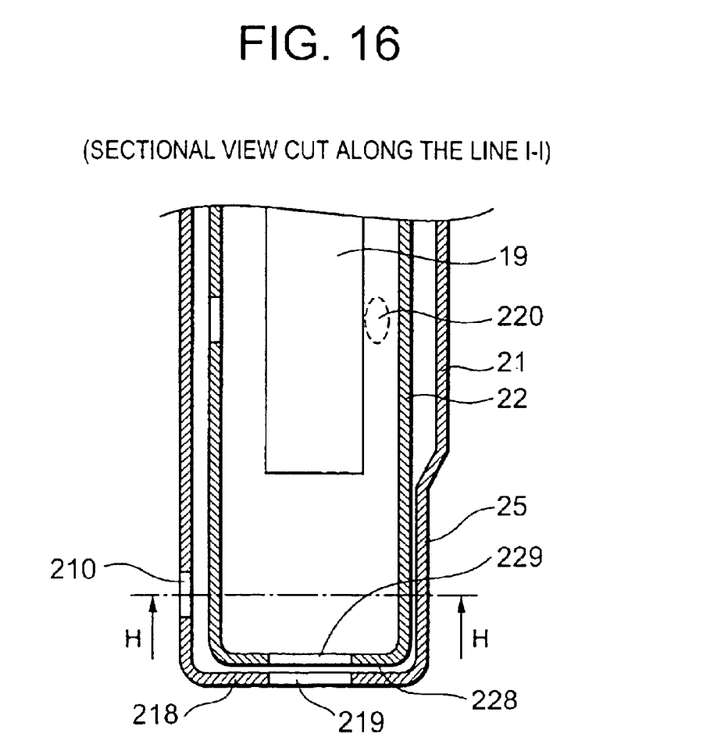
FIG. 16 is an explanatory view in section of essential parts in an axial direction in the vicinity of the measured gas side covers whose four partitions are V-shaped, in an embodiment 5 (sectional view cut along the line I—I of FIG. 17).
Figure 17:
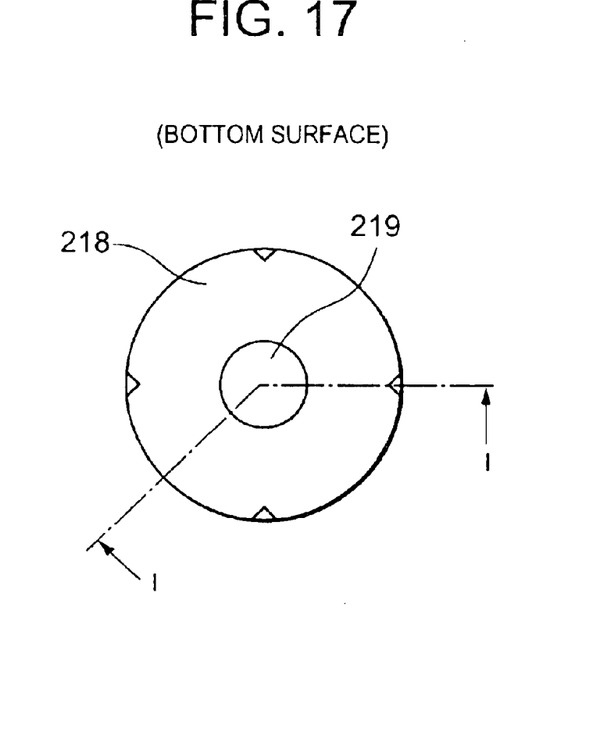
FIG. 17 is a plan view showing the bottom surface of the measured gas side covers in the embodiment 5.
Figure 18:
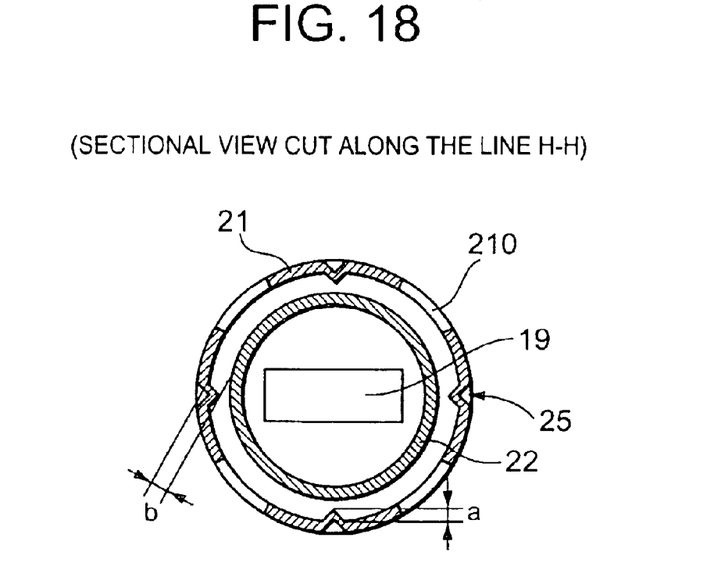
FIG. 18 is an explanatory view in section of the gas sensor in a diametric direction in the embodiment 5 (sectional view cut along the line H—H of FIG. 16).

As shown in FIG. 16 to FIG. 18, in the gas sensor in accordance with the present embodiment, four gas passage holes 210 are provided on the outer cover 21 along the diametric direction, and the partitions 25 are disposed in all parts between the adjacent gas passage holes 210. That is, the number of the partitions 25 is also four. The projection height a of the partitions 25 is 0.8 mm, and the clearance b is 1 mm. The others are the same as in Embodiment 1, and the functional effects are also the same.

What is claimed is:

1. A gas sensor comprising a gas sensor element and a cylindrical housing for inserting and fixing said gas sensor element, a measured gas side cover having a bottom and provided on a tip end side of said housing and an atmosphere side cover provided on a base end side, wherein said measured gas side cover comprises an inner cover for directly covering the gas sensor element, an outer cover directly exposed to measured gas ambience, and a measured gas room inside said inner cover;

gas passage holes for leading a measured gas into said measured gas room are provided on side surfaces of said inner cover and said outer cover respectively, and the gas passage hole provided in said outer cover is disposed in a position much closer to a tip end side thereof than the gas passage hole provided closest to the tip end side in said inner cover;

partitions extending in an axial direction of the gas sensor are provided between said outer cover and said inner cover;

each of said partitions is provided between two adjacent gas passage holes made in said outer cover such that said partitions are circumferentially arranged;

each of said partitions projects in a radial direction of the gas sensor, and a projection height of said partitions is ⅓ or more of a clearance between an inner surface of said outer cover and an outer surface of said inner cover; and an axial length of each of said partitions is ½ or more of an axial length of said gas passage holes made in said outer cover, wherein said partitions are projections provided in circumferential gaps communicating with a plurality of gas passage holes made on the side surface of said outer cover, and these projections provide cuts on part of the side surface of the outer cover, and said partitions are constituted by bending the cut part.

2. The gas sensor according to claim 1, wherein said partitions are constituted to project from said inner surface of said outer cover to said inner cover.

3. The gas sensor according to claim 1, wherein an end portion of said partitions on said base end side in an axial direction of the gas sensor does not reach said gas passage hole provided on said inner cover.

4. The gas sensor according to claim 1, wherein said gas sensor element is board-shaped, and a sectional shape in a diametric direction of said inner cover is elliptic or square.

5. The gas sensor according to claim 1, wherein an axial distance along an axial direction of the gas sensor between the gas passage hole provided closest to the tip end side on said inner cover and the gas passage hole provided closest to the base end side on said outer cover is 5 mm or more.

6. The gas sensor according to claim 1, wherein said outer cover and said inner cover are in a shape having a bottom, and the distance between bottom surfaces of both the covers are in a range of 0 to 5 mm.

* * * * *